United States Patent [19]

Huntress

[11] 4,055,233
[45] Oct. 25, 1977

[54] EAR COUPLER

[75] Inventor: Charles B. Huntress, Orange, Calif.

[73] Assignee: Electronic Engineering Co. of California, Santa Ana, Calif.

[21] Appl. No.: 643,571

[22] Filed: Dec. 22, 1975

[51] Int. Cl.² .................................................. A61B 7/02
[52] U.S. Cl. ..................................... 181/135; 128/152; 179/182 R
[58] Field of Search ..................... 128/152; 179/182 R; 181/129–137

[56] References Cited

U.S. PATENT DOCUMENTS

| 2,573,438 | 10/1951 | Hathaway et al. | 181/130 X |
| 3,415,246 | 12/1968 | Hill | 181/130 X |
| 3,800,791 | 4/1974 | Visor | 181/135 X |
| 3,935,401 | 1/1976 | Shore et al. | 181/135 X |

Primary Examiner—Lawrence R. Franklin
Attorney, Agent, or Firm—Harry R. Lubcke

[57] ABSTRACT

A self-forming ear plug element for use with a stethoscope type sound tube installation for transmitting audio sound to the ear and rejecting ambient noise. A conical portion having a sound-transmitting orifice enters the ear. A thin radially extensive shallow-conical acoustic flange extends outwardly from the major diameter part of the conical portion. Being soft, the flange easily conforms to the concha portion of the ear to increase the sound pressure level of the transmitted signal and to greatly attenuate ambient noise. A mounting horn for attaching the plug element to a stethoscope tube extends axially beyond the flange.

11 Claims, 6 Drawing Figures

EAR COUPLER

BACKGROUND OF THE INVENTION

This invention pertains to acoustic devices of the nature of stethoscopes.

The art is replete with ear tips for stethoscopes; from the simple rounded metal ends of the early doctor's scope to later versions for listening to music or the sounds of motion pictures on airplanes.

For the brief use typical of the doctor, comfort to the wearer is not particularly significant, nor is high attenuation of ambient noise, since the ambient sound level is usually low in a hospital room or a doctor's office.

For use for several hours, as by passengers in an airplane, the prior art has usually supplied a mushroom-shaped semi-stiff cushion having an aperture for resting upon the human ear. The wanted sounds come through the aperture, while the cushion tends to exclude ambient sounds.

Other embodiments have had the shape of an expanding horn, with the large diameter thereof pressing upon the ear. The horn may be made hollow between the inner passage that conducts the wanted sound and the outer surface that assists in reducing ambient noise. This makes the embodiment flexible and so to adapt to the general area of the concha of one's ear with minimum pressure applied by the appliance to the ear.

Still another embodiment is merely a relatively large spongesoft cylinder that remains out of the ear, but deformably rests against it.

Currently available earplugs are generally fabricated from plastics containing plasticizers to promote required flexibility. However, the initial flexibility (a relatively high durometer reading) tends to be too high for comfort. The plasticizer uncontrollably leaches out with time, making the ear plug stiffer and more uncomfortable as time goes on.

BRIEF SUMMARY OF THE INVENTION

The thin radial acoustic flange of this invention is deformed upon the ear plug being placed in the ear. This provides an improved wanted sound pressure level and greater attenuation of ambient noise without requiring uncomfortable pressure upon the ear by the yoke of the stethoscope structure employed. The flange typically has a shallow conical shape disposed away from the ear.

Alternate embodiments include a strictly radial flange, a flange having different thicknesses circumferentially, or different diameters circumferentially.

A further significance of the flange type structure is an increase in the desired sound pressure level and attenuation in the critical speech intelligibility range of audio frequencies, while requiring only 30% to 60% of the pressure against the ear that has usually been employed.

This increases the understandability of motion picture dialogue while offering a high degree of comfort to the wearer, despite hours of wearing the device.

These advantages in frequency response and comfort are sigificant to doctors, also, now that they are available.

The flange, at least is fabricated from a low durometer nonplasticized elastomer. Moulding in a single piece is convenient.

Alternately, the element may be fabricated without a through orifice, in which case it serves as an effective and comfortable ear plug for industrial or aquatic use.

DESCRIPTION OF THE PREFERRED EMBODIMENTS

Figure 1:
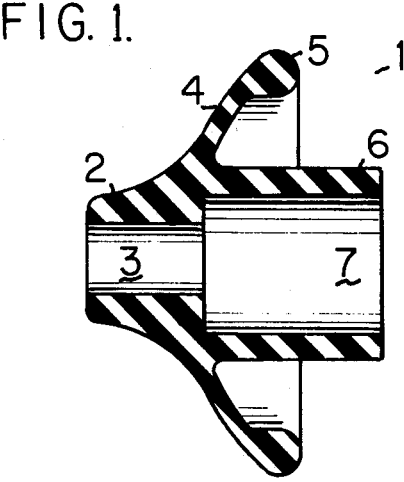
FIG. 1 is a longitudinal sectional view of the ear coupler.
Figure 2:
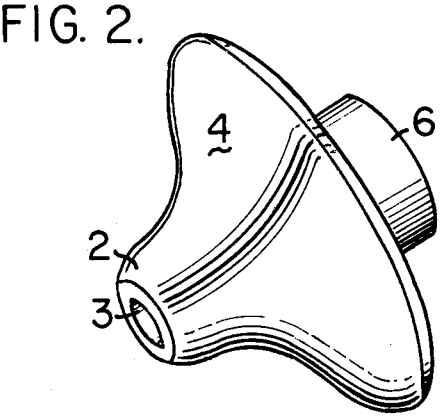
FIG. 2 is a perspective view of the same.

In FIG. 1 numeral 1 indicates an ear coupler as a whole. A conical portion, or ear horn, 2, enters the ear when the device is in use. The length thereof may be about 30% less than the maximum diameter of this truncated conical portion. In a representative embodiment the length is 5 millimeters (mm) and the maximum diameter is 7 mm. Orifice 3 runs axially through the cone and may be 3 mm in diameter.

Acoustic flange 4 is comparatively radially extensive and axially thin with respect to the rest to the coupler in any of the embodiments. It may have a shallow conical shape disposed away from ear horn 2, as shown in FIG. 1. It may have an outer diameter approximating three times the largest diameter of the ear horn, such as having a diameter of 20 mm. The axial thickness may be about ½ mm.

In FIG. 1 a peripheral bead 5 provides nominal peripheral stiffness. This is on the side of the flange away from the ear, and may extend from the flange about 1 mm, increasing the thickness.

In a large measure it is the flexibility of the flange that effects the improved performance of this coupler. Thus, it is fabricated of a very easily deformable rubber, one example of which is silicone rubber. This is preferably very soft, having a Shore A hardness index in the range of 21 to 28.

The silicone material does not employ a plasticizer, such as is required in plastic compositions to give flexibility. Consequently, the ear coupler of this invention does not become less flexible with time. It may also be repeatedly sterilized without losing flexibility.

The conical portion of the ear coupler fits within the ear and provides a clear channel thereinto. This construction has been found to have significance, because other constructions of the prior art, such as the mushroom and cylindrical shapes, tend to exert a closing pressure on the projecting surface of the concha region in the ear canal. This tends to reduce the sound pressure level of the desired sound and also to alter the frequency characteristic of the same, while not giving desired attenuation of ambient noise.

Figure 3:
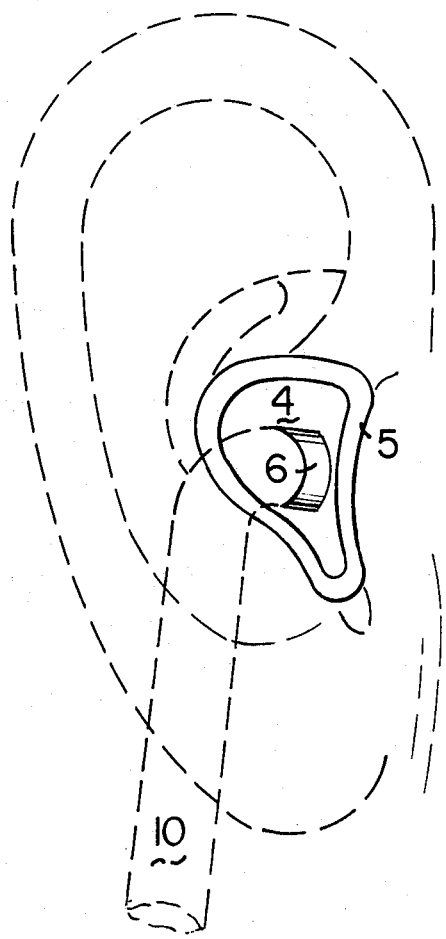
FIG. 3 is a view of the ear coupler in place within an ear.

As shown in FIG. 1, the relaxed configuration of the acoustic flange is that of a shallow cone extending radially from the axis of the coupler. However, in use, significant axial deformation occurs and this causes the flange to intimately lay upon the undulating surface of the concha of the ear. FIG. 3 shows this configuration. It was drawn from a photograph of the coupler in actual use, along with part of a typical yoke, shown dotted.

The flexibility of the flange is great, and so the deformation occurs without discomfort to the wearer. In fact, only about 30 to 60% of the yoke pressure that has been previously employed by the art is required. This may be about 25 grams instead of up to 85 grams for the prior art.

The radial extent of the flange provides a sufficient contact area between the flange and the concha to effectively seal the external portions of the ear from the inner channel of the coupler that carries the wanted sound.

It will be appreciated that this flexible flange mode of sealing is adaptable to almost any ear configuration and nominal range of ear sizes, as from puberty to old age, and considering heredity that might determine the shape, size, and structure of the ear. Further, each time the coupler is used it is self-adjusting and therefore accommodates possible swelling, presence of wax, or any other dimensional change in the concha of a wearer.

For the above reasons it has been found that the coupler of this invention provides superior frequency response for wanted sounds and much greater isolation from unwanted sounds than ear plugs that are even formed specifically for the shape of the ears of a specific wearer.

In the critical speech intelligibility range of from 200 to 1,500 hertz, tests at an independent laboratory revealed a 127% greater desired signal response than the average of six other manufactured couplers of the prior art; also 214% greater attenuation of ambient sound in this range than for the other six couplers.

While acoustic flange 4 has been embodied as having a uniform diameter and uniform thickness, except for peripheral bead 5 heretofore, other embodiments are possible.

Figure 4:
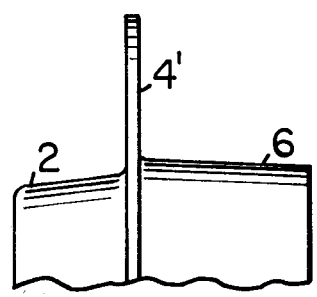
FIG. 4 is a fragmentary view of an alternate embodiment in which the flange is disposed perpendicularly radially outward.

The alternate embodiment of FIG. 4 has a thin flange 4', that, when free, is perpendicularly rather than conically radially outward in its extension from the axis of the coupler. In use in the ear this flange is deformed to an irregular conical shape, similar to the shape taken by prior flange 4, as shown in FIG. 3. The external diameter of flange 4' may be greater than that of flange 4, say 20% greater, in order that the acoustic seal with the concha shall be certain.

The several drawings are approximately 3½ times actual size.

Figure 5:
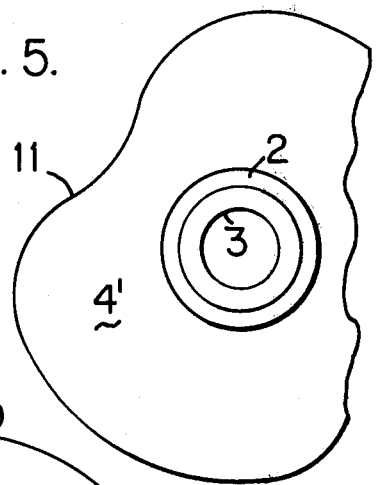
FIG. 5 is a fragmentary view of another alternate embodiment in which the flange has different diameters at different points upon the circumference.

Further, the external diameter of the flanges may vary around the circumference of the flange, as shown in FIG. 5, at 11. This allows the user to match this shape to the concha of the ear as the coupler is inserted.

Figure 6:
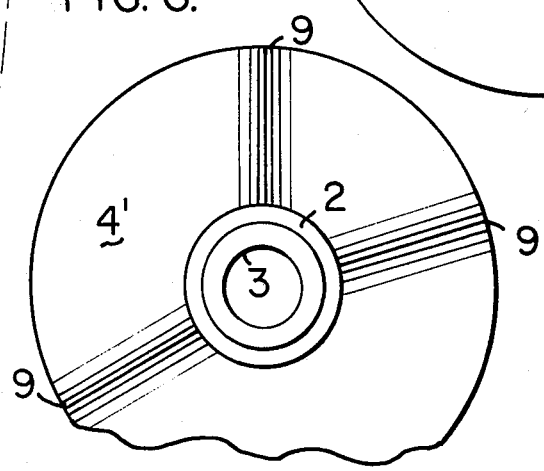
FIG. 6 is a fragmentary view of still another alternate embodiment in which the flange has different thicknesses at different points upon the circumference.

FIG. 6 shows a flange having different thickness at different circumferential positions. This allows the thicker portions 9 to occupy the depressed portion of the concha.

Mounting portion 6 of the coupler extends rearward from flange 4, or 4', thus oppositely from the conical portion. The mounting portion is sometimes termed a "horn", but it does not have the shape nor the function of the horn that is known in acoustic practice.

The mounting portion is typically a cylindrical projection, perhaps slightly larger in diameter than the largest diameter of the conical portion. The cylindrical shape may be modified to have a slight taper that decreases the diameter with distance from the plane of the flange. This is principally for ease in molding the coupler monolithically, and perhaps for aesthetic reasons.

An orifice 7 is provided in the mounting portion. It is typically of larger diameter than the orifice in the conical portion, say 50% larger. This allows the coupler to be mounted on the extremity of a yoke, shown in part in FIG. 3 as 10. The continuing orifice through the yoke and the conical portion of the coupler is thus approximately the same diameter. The yoke, of course, maintains a coupler in each ear mechanically and typically conveys the wanted sound through its hollow interior.

The couplers may be a slip fit upon the yoke so that only new couplers need be supplied for a new wearer. Or the couplers may be mechanically affixed more tightly by appropriate dimensions when the whole is retained intact and disinfected as a whole between wearers.

The use of cement in any part is avoided in the practice of this invention, since it has been discovered that excess cement in obtainable ear coupler - yoke structures has frequently blocked all or a portion of the acoustic orifices thereof.

If the blockage is complete, any stereo effect for music is lost, since the wearer hears through only one ear. It is believed that many lay users do not comprehend that this was happening.

If the blockage is partial the frequency response of the acoustic system is impaired. In one example, this could make dialog less clear in listening to the sound of motion pictures.

I claim:

1. A self-forming ear coupler for acoustic control comprising:
    a. a conical portion, having an orifice therethrough, for entering the ear,
    b. only one soft flexible flange having a shallow conical shape extending outwardly and rearwardly from said conical portion, the external surface of said conical portion and said flange flaring smoothly outwardly to provide a smooth transitional shape therebetween, said flange having a circumferential bead of round cross-section at the outer periphery thereof, the radial extent of said flange being sufficient to effectively seal the external portion of the ear from said conical portion orifice, and
    c. a mounting portion on the side of said flange opposite to said conical portion, said mounting portion having an orifice extending from the orifice of said conical portion to provide a continuous passage through said ear coupler,
    the recited structure being proportioned to significantly deform said flexible flange when it is placed in the ear, whereby said flange acts as an ear plug sealing the ear against ambient sounds.

2. The coupler of claim 1, in which;
    a. the material of which said coupler is formed is an easy deformable silicone rubber.

3. The coupler of claim 1, in which;
    a. the orifice of said conical portion is formed plugged for attenuating all sounds.

4. The coupler of claim 1, in which;
    a. said circumferential bead has a thickness approximately twice as great as the thickness of the flexible flange.

5. The coupler of claim 1, in which;
    a. said orifice in said mounting portion is larger in diameter than said orifice in said conical portion, to accommodate an acoustic tube while maintaining an internal passage of constant cross-sectional area.
6. The coupler of claim 1, in which;
a. said one flexible flange has a diameter of the order of three times that of the largest diameter of said conical portion,
and is circumferentially continuous.
7. The coupler of claim 1, in which;
a. said one soft flexible flange has less than four different diameters that have smooth transitions at different arcs around the circumference thereof
to accommodate the fit into the concha of the ear.
8. The coupler of claim 1, in which;
a. said flexible flange has different thickness at less than eight different segments around the circumference thereof
to accommodate the fit into the concha of the ear.
9. The coupler of claim 1, in which;
a. said conical portion has a length approximately equal to the largest diameter thereof.
10. The coupler of claim 1, in which;
a. the whole structure of said coupler is monolithically cast.
11. The coupler of claim 1, in which;
a. the material of said coupler has a hardness within the range of 21 to 28 on the Shore A hardness scale.

* * * * *